United States Patent [19]
Zupancic et al.

[11] Patent Number: 4,989,849
[45] Date of Patent: Feb. 5, 1991

[54] HEADREST FOR MEDICAL TREATMENT COUCH

[75] Inventors: Anton Z. Zupancic, Kirtland; William H. Amor, Chagrin Falls, both of Ohio

[73] Assignee: Picker International, Inc., Highland Heights, Ohio

[21] Appl. No.: 275,577

[22] Filed: Nov. 23, 1988

[51] Int. Cl.⁵ .............................................. A61G 13/00
[52] U.S. Cl. ................................................... 269/328
[58] Field of Search ................................. 269/322–328

[56] References Cited

U.S. PATENT DOCUMENTS 3,840,221 10/1974 Hogan .................................. 269/322
3,947,686 3/1976 Cooper et al. ...................... 269/322
4,819,925 4/1989 Lunnemann et al. ............... 269/322

Primary Examiner—J. J. Hartman
Attorney, Agent, or Firm—Fay, Sharpe, Beall, Fagan, Minnich & McKee

[57] ABSTRACT

A headrest assembly for a patient receiving couch includes an integrally formed support body and a structure for detachably securing the support body to an associated patient receiving couch. The support body includes a torso receiving region, a neck supporting region and a head receiving region. The securing structure includes a pair of side securing member for positioning a pair of sides of the support body in relation to the patient receiving couch.

12 Claims, 4 Drawing Sheets

HEADREST FOR MEDICAL TREATMENT COUCH

BACKGROUND OF THE INVENTION

This invention generally pertains to patient support structures. More specifically, the present invention relates to a head support structure for positioning the head, neck and torso of a patient's body on a couch or table during medical treatment and diagnosis.

The invention is particularly applicable to a support shell or body which is adapted to support a patient's head, neck and torso during a diagnostic imaging process, such as CT scanning, so that the entire spinal column of the patient can be imaged. However, it will be appreciated by those skilled in the art that the invention has broader applications and may also be adapted for use in other medical treatment and diagnosis environments.

The provision of a simple pillow on a couch to support the head of the patient during diagnostic imaging is not considered adequate because the head of the patient is then not cantilevered out far enough away from the end of the couch to make the entire spine of the patient accessible to diagnostic imaging.

In the medical imaging field, therefore, several types of positioning aid assemblies are known. In one of these, a head support member is rigidly secured to a couch such that the member is not detachable from the couch and so that the member must be used in a given orientation in relation to the couch. In other known types of positioning aid assemblies, the head support is secured to the couch in a tiltable manner. This arrangement is disadvantageous under certain circumstances. In this type of known apparatus, metallic hinges are used to support a plastic head piece. The provision of such hinges is, however, disadvantageous in that the different materials and shapes used for the individual parts of the apparatus cause the imaging radiation to be attenuated in varying degrees depending on the material the radiation passes through.

Another disadvantage of the fixedly installed head supports is that since the head support cannot be removed from the couch or even pivoted out of the way, the couch cannot be used for many diagnostic purposes.

Accordingly, it has been considered desirable to develop a new and improved headrest assembly which would overcome the foregoing difficulties and others, while providing better and more advantageous overall results.

BRIEF SUMMARY OF THE INVENTION

In accordance with the present invention, a headrest assembly is provided for a patient receiving couch.

More specifically, in accordance with this aspect of the invention, the assembly comprises an integrally formed support body comprising a torso receiving region, a neck supporting region, and a head receiving region. A means is provided for detachably securing the support body to an associated patient receiving couch. The means for securing comprises a pair of side securing members for positioning a pair of sides of the support body in relation to the associated patient receiving couch.

In accordance with another aspect of the present invention, a body support structure is provided for patients being exposed to medical radiation. The support structure enables a patient's entire spinal column to be exposed to medical radiation.

More particularly in accordance with this aspect of the invention, the support structure comprises a patient receiving couch and an integrally formed headrest body which is transparent to medical radiation. The body comprises a torso receiving region, a neck supporting region and a head receiving region, which is configured to support a patient's head so as to prevent major head rotations. A means is provided for detachably securing the headrest body to a patient receiving couch. The means comprises a friction pad secured to a lower surface of the torso receiving region.

According to still another aspect of the invention, a headrest assembly is provided which can be selectively secured to a patient receiving couch.

More particularly, in accordance with this aspect of the invention, an integrally formed support body is provided which comprises a torso receiving region, a neck supporting region and a head receiving region. The regions are each configured to respectively support a patient's torso, neck and head. The support body includes first and second plies of a fiber-reenforced plastic material and a reenforcing structure is provided between the plies of material at the neck supporting region. A means for detachably securing the support body to an associated patient receiving couch is also provided.

One advantage of the present invention is the provision of a new and improved headrest assembly.

Another advantage of the present invention is the provision of a headrest shell which is integrally formed, is light and can be easily manufactured and handled.

Still another advantage of the present invention is the provision of a headrest assembly which cantilevers a patient's head far enough past the end of a patient support couch so that the patient's entire spinal column can be exposed to medical radiation.

A further advantage of the present invention is the provision of a headrest assembly which can be selectively detached from an associated patient receiving couch in a simple manner whenever necessary.

A still further advantage of the present invention is the provision of a headrest assembly which absorbs imaging radiation only slightly and in a uniform manner.

A yet further advantage of the present invention is the provision of a headrest assembly which has the necessary rigidity for holding a patient's head without flexing or vibration.

Still other benefits and advantages of the invention will become apparent to those skilled in the art upon a reading and understanding of the following detailed specification.

BRIEF DESCRIPTION OF THE DRAWINGS

The invention may take physical form in certain parts and arrangements of parts, a preferred embodiment of which will be described in detail in this specification and illustrated in the accompanying drawings which form a part hereof, and wherein.

DETAILED DESCRIPTION OF THE PREFERRED EMBODIMENT

Figure 1:
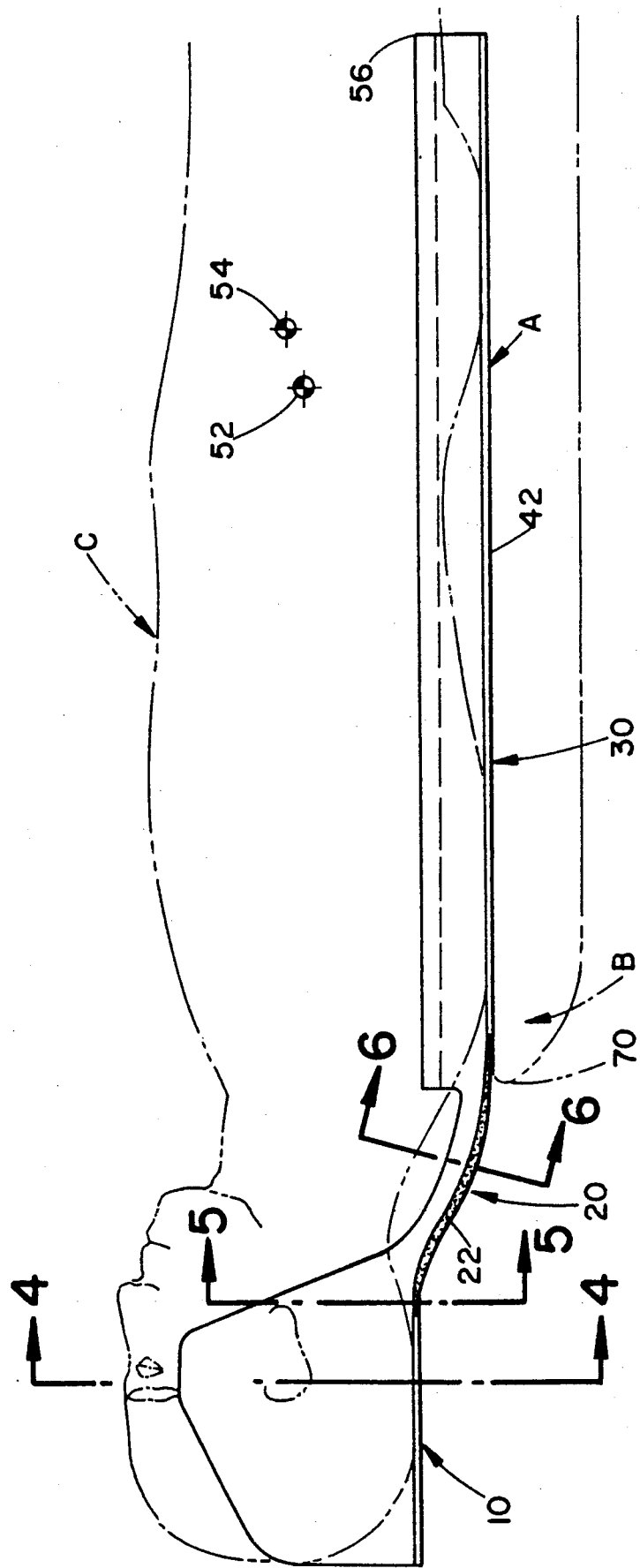
FIG. 1 is a side elevational view, in partial cross-section, of a headrest assembly according to the present invention.

Referring now to the drawings wherein the showings are for purposes of illustrating a preferred embodiment of the invention only and not for purposes of limiting same, FIG. 1 shows the subject new headrest assembly A as positioned on a patient support couch B and supporting a patient C. While the headrest assembly is primarily designed for, and will hereinafter be described in connection with a medical imaging device, such as the CT scanner device D illustrated schematically in FIGS. 2 and 3, it should be recognized that the headrest assembly can be adapted for use in many other patient support environments as well.

Figure 4:
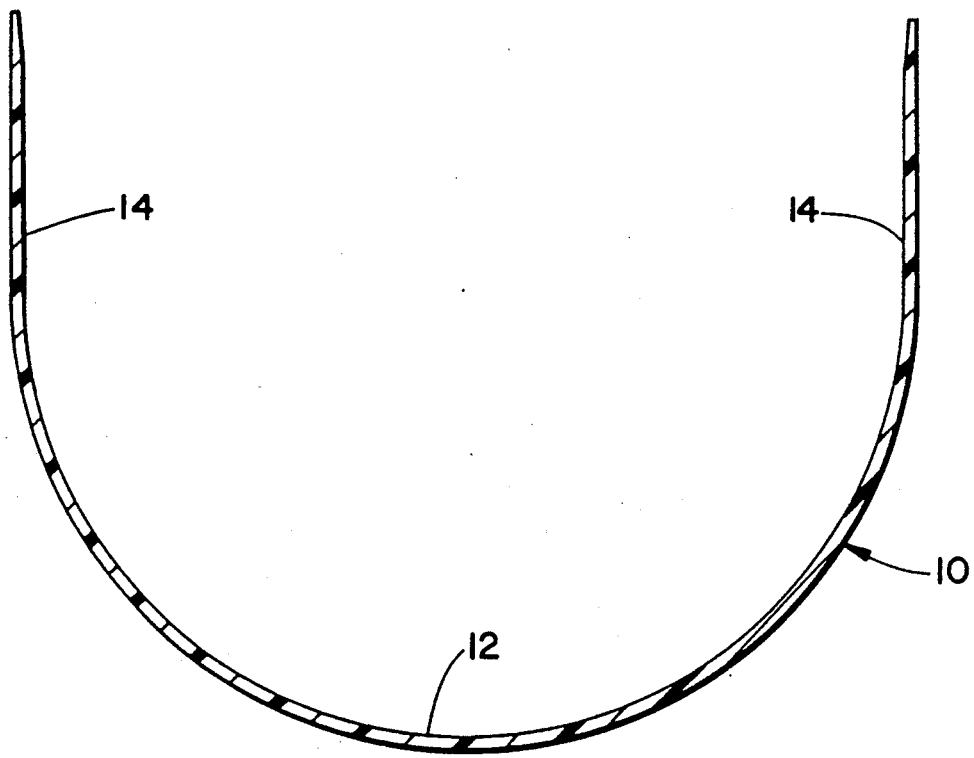
FIG. 4 is an enlarged cross sectional view through the headrest assembly of FIG. 1 along line 4—4.

More specifically, the headrest assembly A comprises a head receiving region 10 which has a base 12 and a pair of side walls 14, as is best illustrated in FIG. 4. The side walls are desirable in order to prevent major movements of the patient's head. For this reason, the region 10 is substantially U - shaped in cross section. As is evident from FIG. 1, the head receiving region 10 is elevated in relation to the rest of the assembly A to comfortably house the head of the patient C.

Figure 6:
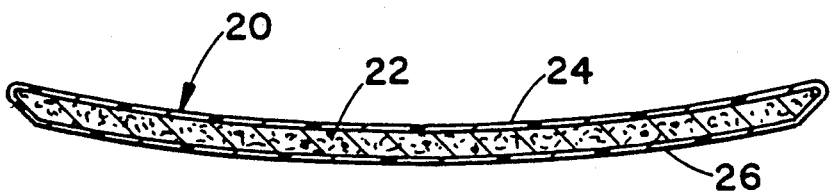
FIG. 6 is an enlarged cross sectional view of the headrest assembly of FIG. 1 along line 6—6; and, FIG. 7 is an enlarged top plan view of a left hand side portion of the headrest assembly of FIG. 3.

The headrest assembly A also comprises a neck support region 20 which includes a reenforcing structure 22, as is more clearly illustrated in FIG. 6. The reenforcing structure 22 is provided between a pair of spaced plies 24 and 26. These plies can each comprise a suitable thermoplastic resin material in which is embedded a mat of support fibers which can be made of a suitable conventional reenforcing material such as a graphite cloth material. The reenforcing structure 22 located between the plies 24, 26, can include a plurality of plies of a biaxial knitted graphite cloth material. It should be recognized, however, that the support structure could also be any suitable type of rigid foam material or even a suitably shaped piece of light wood such as balsa wood. The purpose of the reenforcing structure 22 is to prevent any flexing or vibration or wobbling of the cantilevered head receiving region 10. Such vibration of a patient's head during the imaging process is considered disadvantageous.

Figure 5:
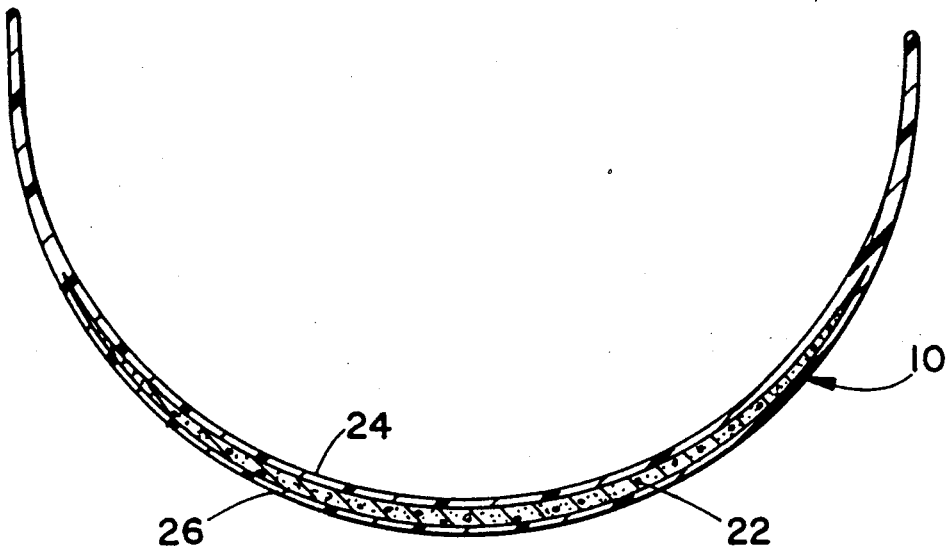
FIG. 5 is an enlarged cross sectional view of the headrest assembly of FIG. 1 along line 5—5.

As is illustrated in FIG. 5, the reenforcing structure 22 extends partially into the head receiving region 10. It can be seen that the two plies 24, 26 become adhered to each other once away from the reenforcing structure 22, as can be seen in the two side walls of FIG. 5. Therefore, the entire structure illustrated in FIG. 4 is comprised of the pair of plies 24, 26 which are adhered to each other so that they lose their separate identities in the FIGURE.

With reference again to FIG. 1, the numeral 30 designates a torso receiving region of the headrest assembly A. As better illustrated in FIG. 2, the torso receiving region 30 is wider than the head receiving region 10 and comprises a base section 32, as well as first and second side flanges 34 and 36 extending from opposing side edges of the base 32. A pair of spaced end flanges 38, 40 are also provided along an end of the torso receiving region adjacent the neck support region 20.

Figure 2:
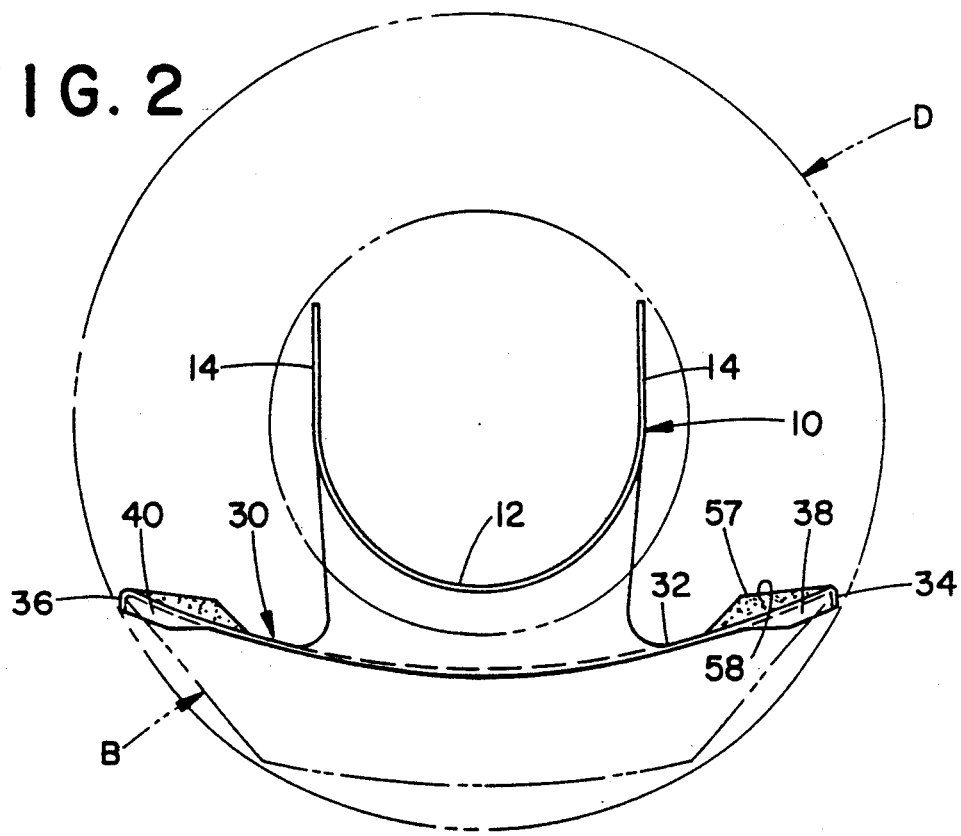
FIG. 2 is an end elevational view of the headrest assembly of FIG. 1 from an upper end thereof.
Figure 3:
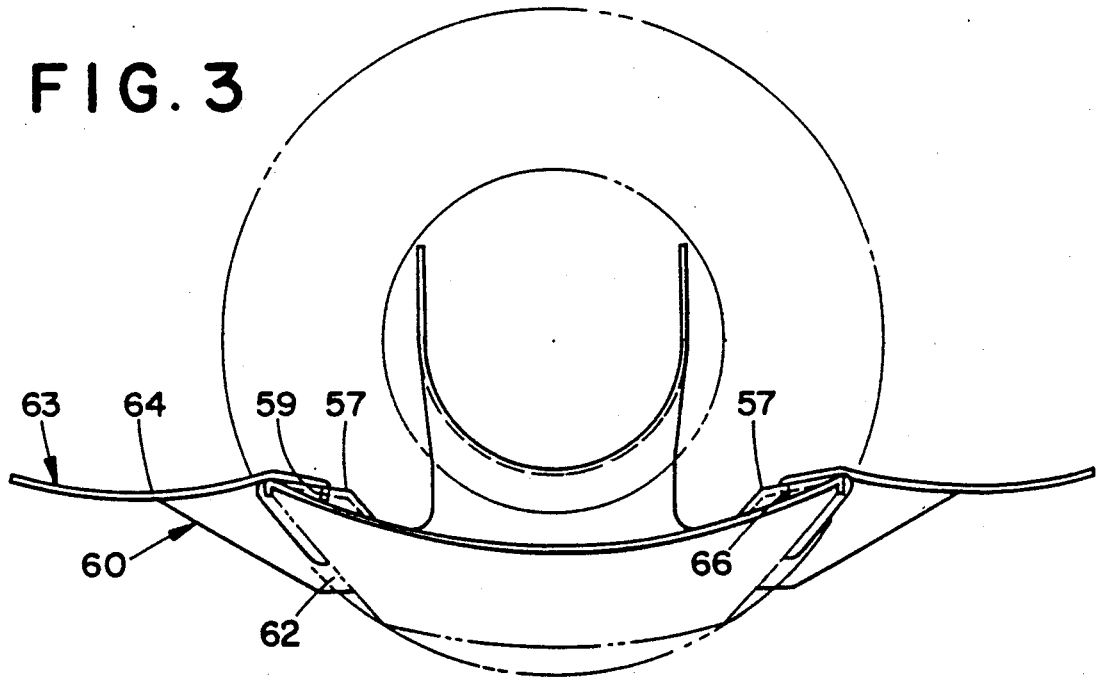
FIG. 3 is an end elevational view of the headrest assembly of FIG. 1 from a lower end thereof with a pair of arm rests attached thereto.

The side flanges 34, 36 and end flanges 38, 40 are adapted to cooperate with the patient receiving couch B in order to secure the headrest assembly A against movement in relation to the couch B. In other words, sideways movement of the torso receiving region 30, and the entire headrest assembly A, is prevented by the side flanges 34, 36 which extend over the side walls of the patient receiving couch B as is best illustrated in FIGS. 2 and 3. Movement of the headrest assembly A toward the right in FIG. 1 is prevented by the provision of the end flanges 38, 40. In order to prevent the movement to the left in FIG. 1, a friction mat 42 is preferably provided between the headrest assembly A and the couch B. Preferably, the friction mat is secured to a bottom surface of the headrest torso receiving region 30. The friction mat can be made of a suitable rubberized polymer material which provides a sticky non-slip surface for the headrest assembly A. Although not illustrated in FIGS. 2 and 3, the friction mat 42 can extend over a substantial portion of the bottom surface of the torso receiving region, if desired.

The torso receiving region 30 is long enough so that the center of gravity of the patient is supported on the headrest assembly A. In this regard, the center of gravity of the 50th percentile of adult males is illustrated by the symbol 52. The 97.5th percentile of center of gravity of adult human males is illustrated by the symbol 54. It can be seen that both of these centers of gravity, 52, 54, are well above a lower end 56 of the torso receiving region 30.

Figure 7:
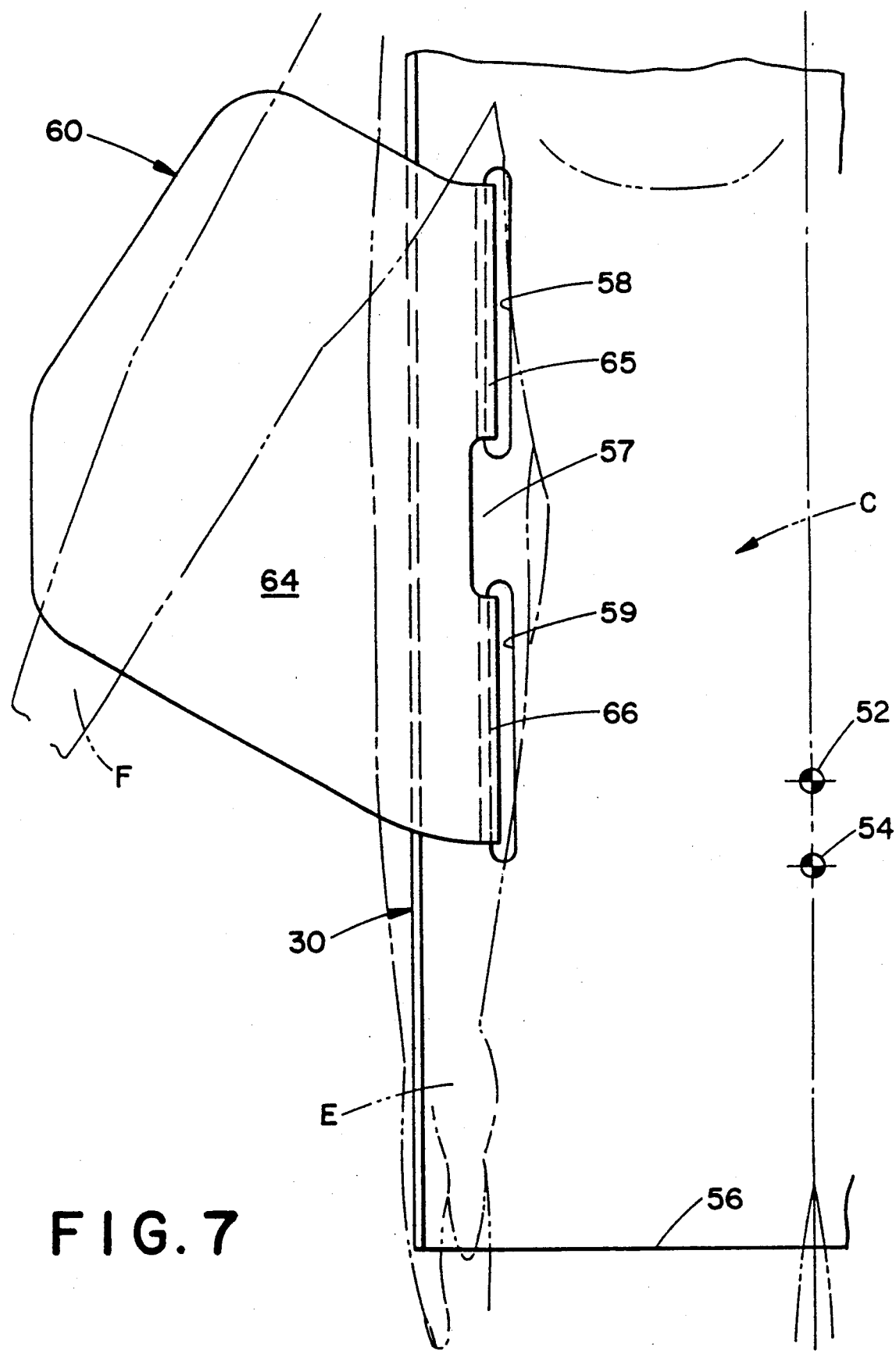

With reference now to FIG. 3, provided adjacent each of the side edges of the torso receiving region 30 is raised section 57. Because the two raised sections 57 are identical, only the left such raised section will be described in this specification, it being recognized that the right raised section has identical functions and features. With reference now also to FIG. 7, the raised section 57 is provided with a pair of longitudinally spaced indented portions 58 and 59. The raised sections 57 are provided along a center portion of the torso section 30 although they are not visible in FIG. 1.

Adapted to cooperate with the raised sections 57 are a pair of arm rests 60 which are detachably secured to the headrest shell A and the couch B. Since the two arm rests are identical, only the left arm rest will be described in detail, it being appreciated that the right arm rest has identical components. The arm rest 60 included a couch contacting portion 62 as well as a top section 63 which is provided with an arm supportion region 64 and a pair of spaced downwardly extending fingers 65 and 66 that are adapted to enter into the pair of indented or depressed portions 58 and 59 (FIG. 7). In this way, the arm rest can be detachably supported in place on the headrest and couch so as to enable a patient to comfortably position his arms during the medical diagnostic process. However, the arm rests can be readily detached when desired.

As is evident from FIG. 7, the arms of the patient can be supported in either of two locations depending upon whether or not the arm rests 60 are secured in place. If the entire spinal column of the patient needs to be imaged then the arm supports cannot be utilized since the torso of the patient will need to enter into the medical diagnostic device D. For this purpose, the arms of the patient can be located at the side of the torso receiving region as is illustrated in dotted lines and identified by the letter E. On the other hand, if only the patient's head and neck need to be imaged, the patient's arms can be placed more comfortably on the arm supports as is identified bY the letter F.

Since the arm rests 60 will not be exposed to imaging radiation because, as mentioned, the arm rests will be detached if the torso of the patient is to be imaged, the arm rests do not have to be made from a relatively thin material which will absorb imaging radiation in a uniform matter. All that is necessary is that the arm rests be capable of supporting the patient's arms without much flexing. For this reason, the arm rests can be made of any suitable material such as a conventional plastic material.

The headrest assembly A of the present invention is advantageous in that it can cantilever the head of the patient out away from an end 70 of the couch B far enough so that the entire spine of the patient is imagable with a conventional medical diagnostic apparatus D. Additionally, the headrest assembly A selectively hooks onto the couch B to prevent movement of the assembly sideways. The friction mat 42 and the end flanges 38, 40 prevent movement of the headrest assembly lengthwise. However, the entire assembly can be lifted away from the couch B so that the couch can then be used for other medical purposes.

Because the assembly A is a unitary shell-like article made from a fiber reinforced plastic material, it will absorb imaging radiation in a uniform manner. Since the headrest assembly is quite thin, being approximately 0.1 cm in thickness, except in the neck region where it is approximately 0.25 cm in thickness, it will absorb only a slight amount of radiation. In the preferred embodiment, the assembly A is 16.66 cm wide in the torso receiving region. The length of the assembly A is approximately 40 cm. As is evident from the FIGURES, the assembly is arcuate in a cross-section transverse to its longitudinal axis so as to conform to the shape of the couch B.

The invention has been described with reference to a preferred embodiment. Obviously, alterations and modifications will occur to others upon a reading and understanding of this specification. All such modifications and alterations are intended to be included insofar as they come within the scope of the appended claims or the equivalents thereof.

Having now described the invention, what is claimed is:

1. An upper body support structure for patients undergoing radiographic, diagnostic examination of head and spinal column regions, the structure comprising:
   an integrally formed, unitary upper body support member which is transparent to diagnostic radiation, the member including:
   a torso receiving region having an upper portion, said torso receiving region being which is dimensioned to slide between a flat upper surface of a patient supporting couch and a patient laying on the couch in a prone position without requiring the patient to sit up, roll-over, or bend its spinal column, the torso receiving region defining a pair of indented portions adjacent upper portion side edges thereof, each indented portion having a generally vertical surface disposed adjacent one side edge of the torso receiving region,
   a neck region connected integrally with the upper portion of the torso receiving region and extending upward therefrom along a generally arcuate path,
   a head receiving region integrally formed with the neck region to support the patient's head in a prone position, the head receiving region including side members for inhibiting head rotation and preventing the patient's head from sliding off the head receiving region;
   a pair of arm supports, each arm support including (i) a downward extending detent having a generally vertical surface for frictionally engaging the torso receiving region indented portion generally vertical surface, (ii) a downward depending foot portion for abutting a side surface of the patient receiving couch, and (iii) an arm supporting surface which is mounted in a generally horizontal position when the generally vertical surfaces are frictionally engaged and the foot portion is pressing against the vertical side surface of the couch; and
   wherein the torso receiving region extends between the patient and the couch at least beyond a center of gravity of the patient, such that the torso receiving region is urged firmly against the patient couch upper surface by the patient's weight when the neck and head regions are cantilevered over an end of the couch.

2. The structure as set forth in claim 1 wherein the head receiving region is substantially U-shaped in a cross section transverse to a longitudinal axis of the torso receiving region.

3. The structure as set forth in claim 1 further including a pair of downward projecting stops integrally connecting adjacent the upper portion of the torso receiving region for selectively engaging a vertical surface of the patient couch for limiting sliding receipt of the structure between the patient and the patient couch upper surface.

4. The structure as set forth in claim 1 wherein the neck receiving region includes an upper surface portion of an integral, unitary construction with the torso and head regions and a lower surface portion which is an integral unitary structure with the torso and head receiving region and further including a rigid spacing structure for holding the upper and lower surfaces in a fixed, space relationship, such that the upper and lower surfaces and the spacing means define a truss-like assembly which adds rigidity to the neck supporting region.

5. An upper body supporting structure for a patient disposed on a patient couch for supporting the patient's head and spinal column during a radiographic, diagnostic examination, the structure comprising:
   a torso receiving region which is generally linear in longitudinal direction and has an arcuate contour in a transverse direction, the torso receiving region having a first end which is disposed adjacent a first end of the patient couch generally under the patient's shoulders with the patient's head and neck cantilevered over the couch first end, such that the torso receiving region is urged firmly against the patient couch upper surface by the patient's weight when the neck and head regions are cantilevered over an end of the couch, the torso receiving region having a second end disposed a sufficient distance from the torso receiving region first end to extend past a center of gravity of a patient supported on the patient couch with its shoulders adjacent the couch first end, the torso receiving region being horizontally slidably received from the couch first end between a couch upper surface and the patient;

a friction pad mounted between a lower surface of the torso receiving region and the patient couch for inhibiting sliding and movement therebetween;

a neck region of the low friction plastic polymer integrally connected with the torso receiving region first end in a unitary, one piece configuration;

a head region of the plastic material integrally connected to the neck region in an integral, one piece configuration, the head and neck regions being cantilevered over the couch first end.

6. An upper body supporting assembly which can be selectively supported on a patient couch, the assembly comprising:

a torso receiving region constructed of a radiation transmissive polymer and slidably receivable along and generally confirming with an upper surface of the couch, the torso receiving region being constructed of a radiation transmissive polymer;

a neck region including an upper surface portion constructed of the radiation transmissive polymer and integrally connected with the torso receiving region to define a unitary structure, a lower surface portion extending below and spaced from the upper surface portion, the lower surface portion being constructed of the radiation transmissive polymer and integrally connected with the torso receiving region in a unitary, one piece construction;

a head region constructed of the radiation transmissive polymer and integrally connected with the upper and lower surface portions of the neck supporting region in an integral unitary, one piece construction;

a rigid material connected between the upper and lower surface portions for rigidly holding the upper and lower surface portions in a rigid, fixed relationship, the reinforcing material being connected with the upper and lower surface portions to inhibit relative movement therebetween; and wherein the torso receiving region extends between the patient and the couch at least beyond a center of gravity of the patient, such that the torso receiving region is urged firmly against the patient couch upper surface by the patient's weight when the neck and head regions are cantilevered over an end of the couch.

7. The assembly as set forth in claim 5 wherein the rigid material includes a plurality of plies of a radiation transmissive cloth material.

8. The assembly as set forth in claim 6 wherein the reinforcing material includes a rigid foam material.

9. An upper body supporting assembly which can be selectively supported on a patient couch, the assembly comprising:

a torso receiving region which is generally linear in longitudinal direction and has an arcuate contour in a transverse direction, the torso receiving region having a first end which is disposed adjacent a first end of the patient couch generally under the patient's shoulders with the patient's head and neck cantilevered over the couch first end, the torso receiving region having a second end disposed at least beyond a center of gravity of the patient, such that the torso receiving region is urged firmly against the patient couch upper surface by the patient's weight when the neck and head regions are cantilevered over an end of the couch, the torso receiving region being horizontally slidably received from the couch first end between a couch upper surface and the patient;

a friction pad mounted between a lower surface of the torso receiving region and the patient couch for inhibiting slide and movement therebetween;

a neck region including an upper surface portion constructed of the radiation transmissive polymer and integrally connected with the torso receiving region to define a unitary structure, a lower surface portion extending below and spaced from the upper surface portion, the lower surface portion being constructed of the radiation transmissive polymer and integrally connected with the torso receiving region in a unitary, one piece construction;

a head region constructed of the radiation transmissive polymer and integrally connected with the upper and lower surface portions of the neck supporting region in an integral unitary, one piece construction;

a rigid material connected between the upper and lower surface portions for rigidly holding the upper and lower surface portions in a rigid, fixed relationship, the reinforcing material being connected with the upper and lower surface portions to inhibit relative movement therebetween.

10. The assembly as set forth in claim 9 further including a pair of arm supports, each arm support including a downward extending detent having a surface for frictionally engaging a torso receiving region indented portion generally vertical surface, (ii) a downward depending foot portion for abutting a side surface of the patient receiving couch, and (iii) an arm supporting surface which is mounted in a generally horizontal position when the detent and indent surfaces are fictionally engaged and the foot portion is pressing against the vertical side surface of the couch.

11. The assembly as set forth in claim 9 wherein the head receiving region is substantially U-shaped in cross section transverse to a longitudinal axis of the torso receiving region.

12. The assembly as set forth in claim 9 further including a pair of downward projecting stops integrally connected adjacent an upper portion of the torso receiving region for selectively engaging a vertical end surface of the patient couch for limiting sliding receipt of the structure between the patient and the patient couch upper surface.

* * * * *